United States Patent [19]

Senior

[11] Patent Number: 5,504,013
[45] Date of Patent: Apr. 2, 1996

[54] ANALYTICAL DEVICES AND METHODS OF USE THEREOF

[75] Inventor: Stephenie J. Senior, Bedford, United Kingdom

[73] Assignee: Unipath Limited, Hampshire, England

[21] Appl. No.: 338,150

[22] Filed: Nov. 9, 1994

[30] Foreign Application Priority Data

Nov. 12, 1993 [EP] European Pat. Off. ............. 93309055

[51] Int. Cl.[6] ..................... G01N 33/558; G01N 33/543; G01N 33/76
[52] U.S. Cl. ............... 436/165; 422/56; 422/58; 422/61; 436/169
[58] Field of Search ................. 422/56, 58, 61; 436/169, 165

[56] References Cited

U.S. PATENT DOCUMENTS

| | | | |
|---|---|---|---|
| 3,620,677 | 11/1971 | Morison | 422/56 |
| 3,642,450 | 2/1972 | Eriksson | 422/61 |
| 3,768,979 | 10/1973 | Mead et al. | 422/61 |
| 3,980,436 | 9/1976 | Greenfield et al. | 422/61 X |
| 4,258,135 | 3/1981 | Meunier | 422/61 X |
| 4,624,929 | 11/1986 | Ullman | 422/61 X |
| 4,635,488 | 1/1987 | Kremer | 422/58 X |
| 4,678,757 | 7/1987 | Rapkin et al. | 422/58 X |
| 4,960,691 | 10/1990 | Gordon et al. | 422/58 X |
| 5,275,785 | 1/1994 | May et al. | 422/58 X |

FOREIGN PATENT DOCUMENTS

| | | |
|---|---|---|
| 0383619 | 8/1990 | European Pat. Off. . |
| 2204398 | 11/1988 | United Kingdom . |
| 9303673 | 3/1993 | WIPO . |

OTHER PUBLICATIONS

Database WPI, Week 8828, Derwent Publication Ltd., London, GB; AN 88-195635, 7 Jun. 1988.

Database WPI, Week 8748, Derwent Publications Ltd., London, GB; AN 87-339223, 26 Oct. 1987.

*Primary Examiner*—James C. Housel
*Assistant Examiner*—Arlen Soderquist
*Attorney, Agent, or Firm*—Cushman Darby & Cushman

[57] ABSTRACT

An analytical device for determining the presence and/or concentration of an analyte in a sample liquid comprises a hollow casing; an assay strip within said casing for selectively capturing an analyte in sample liquid applied to the device; a bibulous sample liquid receiving member at or adjacent to a first extremity of said casing which collects sample liquid and transports it into the casing; a window in the casing at a location remote from the first extremity of the casing; and a single cap which can be applied in turn over the window during sample collection, and then over the sample receiving member.

9 Claims, 2 Drawing Sheets

ANALYTICAL DEVICES AND METHODS OF USE THEREOF

This invention relates to the construction and use of analytical devices, especially those adapted for use by relatively unskilled persons for example in the home.

Home-use devices for the analysis of urine, for example in pregnancy tests and ovulation prediction tests, are now widely available commercially. Many such devices are based on the principles of immunochromatography, and typically comprise a hollow casing constructed of plastics material containing a porous assay strip carrying pre-dosed reagents. The user merely needs to apply a urine sample to one part of the casing to initiate the assay. The assay result becomes visible by eye within a few minutes without further action by the user. Examples of such devices are described in EP-A-291194 and EP-A-383619.

Sample collection is conveniently achieved by means of a bibulous member which forms part of the device and which can readily take up sample liquid, e.g. from a urine stream. Optionally the bibulous member can protrude from the casing of the device to facilitate sample application. In any event, the bibulous member is normally located at or near an extremity of the device so that the bibulous member can be introduced into a source of sample liquid, such as a urine stream, while minimising the likelihood of direct contact between the sample liquid and the hands of the user. Devices of this type are sometimes supplied with a cap which the user can place over the bibulous member after sample application. The benefits of the cap are primarily hygienic.

In order to reveal the assay result, the casing of the device has one or more apertures or windows through which the interior of the device can be observed. At the very least, the efficiency of the device is impaired if sample liquid enters the device through such observation windows. Desirably the only route of access by the sample liquid into the interior of the device is via the bibulous receiving member. In an attempt to minimise the risk of ingress of sample liquid through such observation windows, several commercial devices incorporate transparent sheet material located against the interior or exterior of the window, to act as a seal.

The invention provides an analytical device for determining the presence and/or concentration of an analyte in a sample liquid, comprising:

a hollow casing;

means within said casing for selectively capturing said analyte in sample liquid applied thereto;

a bibulous sample liquid receiving member at or adjacent to a first extremity of said casing, said receiving member providing means for collecting sample liquid and transporting collected sample liquid into said casing;

window means in said casing at a location remote from said first extremity of said casing, said window means enabling detection of said analyte to be effected from outside said casing;

cover means engageable with said casing to enclose and seal said bibulous sample receiving member from contact with the surrounding environment; and cover means releasably engageable with said casing to enclose said window means.

Preferably, in the interests of economy of materials and to minimise environmental impact, only a single cover means is provided, said single cover means being arranged to enclose said bibulous sample receiving member and said window means but not both simultaneously.

Desirably, said cover means provide(s) means for handholding said device while either or both of said bibulous sample receiving member and said window means are enclosed thereby.

In a particularly convenient form of the invention, said casing is elongate and said first extremity is one end thereof. In this embodiment, it is preferable that said cover means is/are telescopically receivable over either or both ends of said elongate casing.

The analytical devices of the invention provide a number of advantages over devices of the prior art:

a) The device can be made smaller without loss of hygiene and convenience for the user, or loss of accuracy of the assay result. Indeed, accuracy may be improved. Because the observation window is enclosed during collection of the sample, the observation window can be located much closer to the sample collector. If the assay device comprises an assay strip within the casing, the working length of the strip can be shorter and the speed and accuracy of the test improved. A smaller device may be made more cheaply because it requires less raw material.

b) The device can be provided to the user in a form which is immediately ready for use. The device can be provided wrapped inside a moisture-impervious pouch or sachet which can, for example, be simply torn open in the conventional manner to release the device. On opening the pouch, the device is found with the cover means enclosing the observation window and the bibulous sample collector exposed. After sample collection, the cover means can immediately be placed over the sample collector to seal it.

By requiring that the cover means, e.g. cap, should "seal" the bibulous sample receiving member from the surrounding environment after sample collection, we do not mean that the enclosure of the receiving member should necessarily be totally hermetic. However, the sample receiving member should be sufficiently enclosed by the cover means to prevent gross loss of moisture by dripping or liquid flow into external objects such as fabrics into which the non-enclosed sample receiving member might come into contact. In addition, the likliehood of loss of moisture by evaporation into the surrounding atmosphere from the sample receiving member should be substantially reduced under normal conditions of temperature and humidity likely to be encountered during use. Preferably, to the extent that this is practicable using conventional materials such as plastics and conventional moulding techniques, the sealing of the sample receiving member by the cover means should be essentially hermetic.

At the present time, commercially available home-use diagnostic devices generally provide the assay result in qualitative or semi-quantitative terms only. For example, a pregnancy test only needs to give a "yes/no" result. However, there is a desire to adapt the home-use technology to more sophisticated uses. An example is in the monitoring of the human ovulation cycle to provide more accurate status information which can be used to assist conception, or indeed to facilitate contraception. This can best be achieved on the basis of accurate numerical data. Proposals have been made to utilise changes in analyte levels in body fluids, especially hormone metabolites in fluids such as urine and saliva, to indicate the changing status of the ovulation cycle. Frequent, e.g. daily, testing of body fluid samples is needed. Calculation and interpretation of the individual assay results typically require the use of an electronic device such as a microprocessor. It is generally envisaged that whereas the microprocessor or similar unit will be retained for a long time by the user, the testing of body fluid samples will be conducted using a plurality of disposable testing devices which are used only once and then thrown away.

Hence, during the repetitious assay procedure, a disposable analytical device will be used to sample the body fluid and to perform the basic assay. Thereafter the user will present the disposable device to the permanent reader/microprocessor in order for the individual assay result to be recorded and interpreted. Typically this may involve engagement or insertion of a portion of the disposable device into a slot or other shaped orifice in the structure of the reader/microprocessor, to facilitate positive location of the disposable device in relation to a reading head which forms part of the reader/microprocessor. Because the reader/microprocessor is an item of equipment which the user must retain for repeated use, it is easy to imagine that the user may have misgivings about such a procedure. The exterior of the disposable analytical device may easily become contaminated with sample fluid. Such contaminating fluid might be transferred to the permanent reader/microprocessor, and for reasons of hygiene there may be reluctance to retain and re-use such a contaminated item. We believe that in order to promote consumer acceptance of such an analytical system, it is necessary to minimise the likelihood of sample contamination on the portion of the disposable assay device which is to be engaged with the reader/microprocessor.

Moreover, if body fluid is transferred therefrom into the reader/microprocessor, it may interfere with the accurate performance of the reader/microprocessor, especially if it accumulates therein or dries thereon to leave a deposit that is difficult to remove.

If an analytical device of the invention is to be used in conjunction with a separate reading device, such as an electronic reader than can interpret the result of an assay performed within the analytical device, it is convenient if said window means is located in a portion of said casing which is cooperatively engageable with means for reading the result of the analysis, said cooperatively engageable portion becoming exposed when said cover means is released to expose said window means.

The invention also provides advantageous ways of obtaining and assaying sample liquids, such as body fluids, using an analytical device according to the invention as described above, wherein during sample collection involving introduction of said bibulous sample receiving member into a source of sample liquid said device is hand-held by means of said cover means enclosing said window means, and thereafter said cover means is released to expose said window means. Preferably, after release of said cover means to expose said window means, the same cover means is used to enclose said bibulous sample receiving member. Preferably, following sample collection and enclosure of said bibulous sample receiving member, said device is hand-held by means of said cover means enclosing said bibulous sample receiving member, for example to facilitate presentation of said window means to means for reading the result of said analysis.

By way of example only, a preferred embodiment of the invention is now described with reference to the accompanying drawings, which show:

BRIEF DESCRIPTION OF THE DRAWINGS

Referring to FIG. 1, the device comprises a casing 10 having upper and lower halves 11 and 12. The casing is of elongate form and has a rectangular lateral cross-section. At each longitudinal end of the casing, this lateral cross-section is reduced in a single step down to provide two opposing extremities of the casing, each of which can accommodate a cap which can fit telescopically over the extremity and butt against the central portion of the casing. The lateral cross-section of each extended portion 13 and 14 of casing 10 is the same, permitting a single cap 15 to be fitted over either extended portion. Extended portion 13 partially encloses a protruding bibulous member 16 which can act as a receiving member for applied sample fluid such as urine. Protruding bibulous member 16 and extended portion 13 can both be accommodated within the cap 15 when the cap is telescopically fitted over portion 13 of the casing. Extended portion 14 of the opposite end of the casing incorporates a reading window through which an assay result can be detected. Reading window 17 is seen on the upper surface 18 in FIG. 1.

Referring to FIG. 2, the assay device is seen from above with cap 15 fitted telescopically over extended portion 14. Extended portion 13 and the bibulous sample receiving member 16 are exposed. Sample liquid 20 can be applied to the receiving member 16.

Referring to FIG. 3, after sample collection, cap 15 can be removed from extended portion 14 and telescopically applied to extended portion 13. In this configuration cap 15 encloses both extended portion 13 and the now-moistened sample receiving member 16, sealing the sample receiving member from the surrounding environment. Extended portion 14 including the reading window 17 is now exposed. An assay result (depicted as a line 30 in FIG. 3) can be observed through reading window 17.

Figure 2:
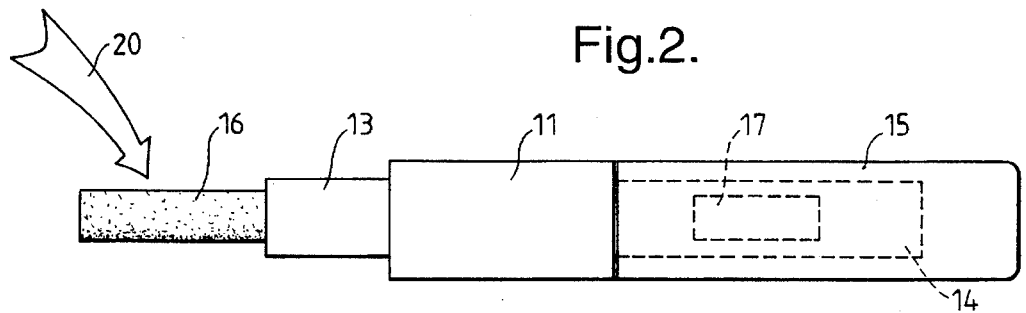
FIG. 2: A view of the device of FIG. 1 seen from above with the cap placed over the window means.

During sample collection (FIG. 2) the device can conveniently be held by means of cap 15 located over extended portion 14. The fingers of the user are therefore well separated from the sample receiving member 16 in contact with the sample source, such as a urine stream. Following sample collection the device may be briefly held by means of the central portion 11 while cap 15 is removed and fitted over extended portion 13 and receiving member 16. The sample-moistened receiving member 16 is therefore hygienically enclosed within the cap 15, and the extended portion 14 containing the reading window has during sample collection been protected from contact with any sample liquid. Loss of moisture into the environment from member 16 by dripping, capillary flow or evaporation is minimised. After telescopically applying cap 15 over receiving member 16, as seen in FIG. 3, the device can be held cleanly by cap 15 and the extended portion 14 with the reading window 17 can be presented to a separate reading device which can evaluate the assay result.

Figure 3:
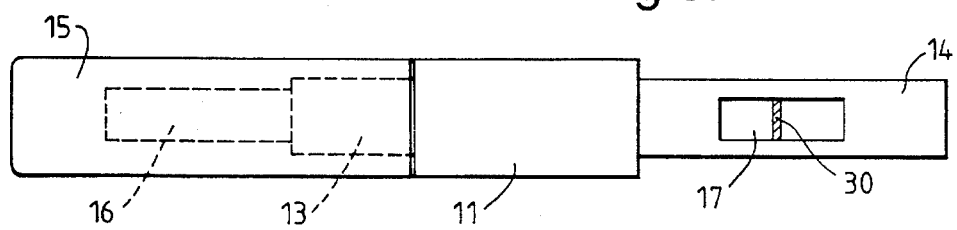
FIG. 3: A view of the device of FIG. 1, again seen from above, but with the cap removed and replaced over the sample collector.
Figure 4:
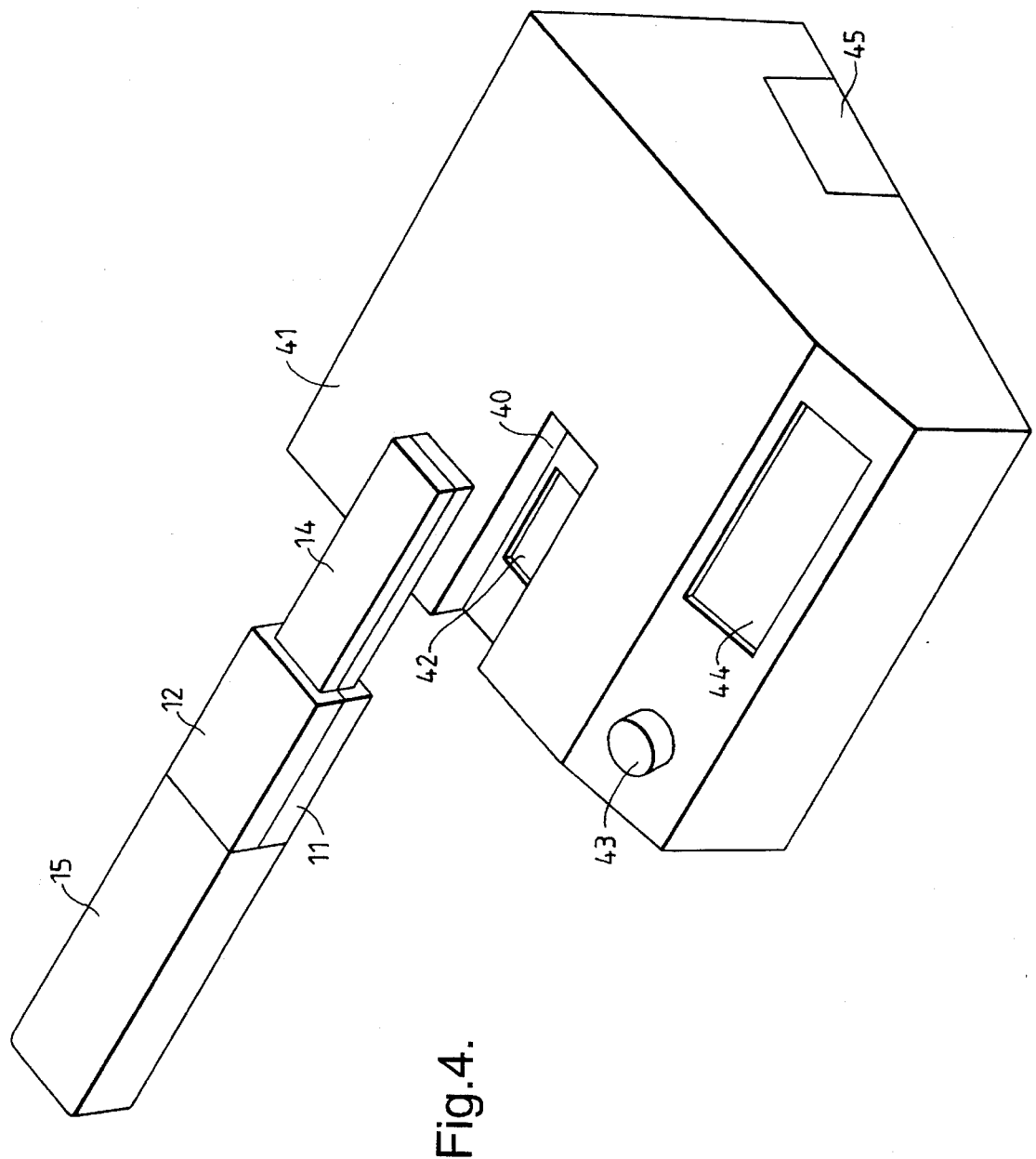
FIG. 4: A general view of the device of FIG. 1 being engaged with a reading device.

This final action is depicted in FIG. 4, which shows the reading device as seen in FIG. 3 inverted so that the reading window is now on the underside of extended portion 14. Extended portion 14 is being located in a recess 40 of a reader/monitor 41. Within recess 41 is a reading sensor (represented by window 42) which when the testing device is properly inserted in the recess is adjacent to the reading window 17 of the assay device. The exterior of the casing of reader 41 can incorporate other features such as operating controls 43, a visual output 44, such as a liquid crystal display panel, and access 45 to the interior of the device e.g. for battery replacement.

Figure 1:
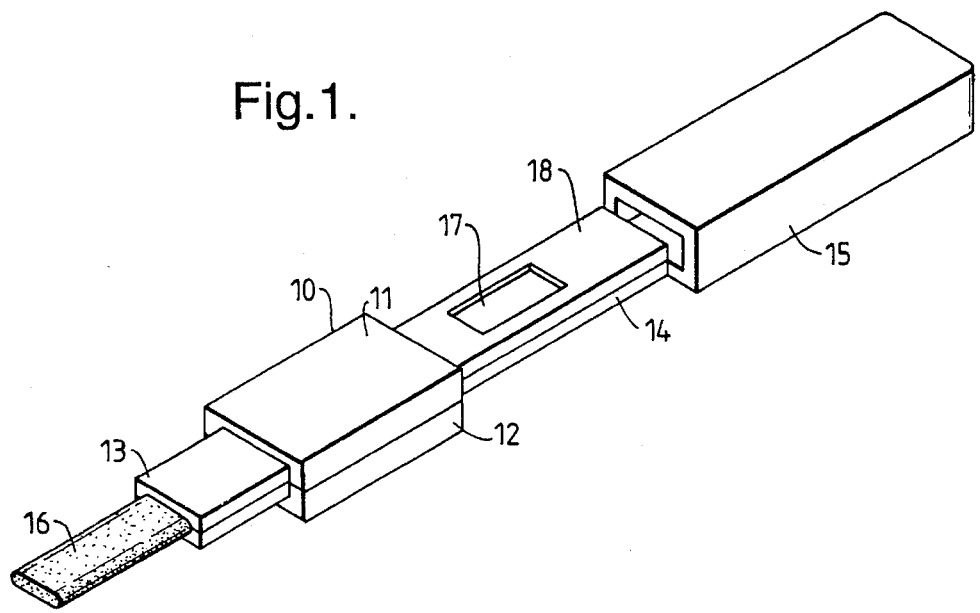
FIG. 1: A general view of an analytical device in accordance with the invention together with an associated cap.

The device of FIG. 1 can conveniently be made from plastics (e.g. polystyrene) mouldings, with the upper and lower halves of the casing sealed together if necessary, for example by ultrasonic welding. The interior of casing 10 can contain a porous carrier strip extending from portion 13 of the casing along the length of the casing and past reading window 17. Access of liquid sample to the porous strip within the casing should only be effected via sample receiving member 16, and this is greatly facilitated by the fact that cap 15 encloses reading window 17 during sample collection. Cap 15 can be a separate single plastics moulding. The outer casing of reader 41 can also be easily manufactured from one or more plastics mouldings.

The skilled reader will appreciate that the detailed construction of the device within casing 10 is not critical to the present invention. Neither are the electronic or other constructional features within the casing of reader 41.

It will be appreciated that the overall shape and dimensions of casing 10 and cap 15 can be subject to considerable variation from that described above without departing from the principles of the invention. Similarly the interactive shapes of portion 14 and the recess or other engaging location in the reader casing can be varied. Purely by way of example of such immaterial variations that may be made:

a. Sample collector 16 may be contained wholly within extended portion 13 and only accessible to applied liquid sample via one or more apertures in portion 13.

b. Extended portion 14 can contain more than one reading window if desired, and the assay result can be displayed in any machine-readable form.

c. When the assay device is supplied to the consumer, cap 15 may be already fitted to the device or may be supplied separately.

d. The assay device may have any lateral cross-section or shape, such as circular or oval, which is convenient to manufacture, and convenient to hold during use.

I claim:

1. An analytical device for determining the presence and/or concentration of an analyte in a sample liquid, comprising:

a) a hollow casing;

b) a bibulous sample liquid receiving member at or adjacent to a first extremity of said casing, said receiving member providing means for collecting sample liquid and transporting collected sample liquid into said casing;

c) means within said casing for selectively capturing said analyte in said collected sample liquid;

d) window means in said casing at a location remote from said first extremity of said casing, said window means enabling detection of said analyte to be effected from outside said casing; and e) a single cover means engageable with said casing to enclose said bibulous sample receiving member and releasably engageable with said casing to enclose said window means, but not engageable with said casing to enclose both of said bibulous sample receiving member and said window means simultaneously.

2. An analytical device according to claim 1, wherein said cover means provides means for hand-holding said device while either of said bibulous sample receiving member and said window means are enclosed thereby.

3. An analytical device according to claim 1, wherein said casing is elongated and said first extremity is one end thereof.

4. An analytical device according to claim 3, wherein said cover means is telescopically receivable over each end of said elongate casing.

5. An analytical device according to claim 1, wherein said window means is located in a portion of said casing which is cooperatively engageable with means for reading the result of the analysis, said cooperatively engageable portion becoming exposed when said cover means is released to expose said window means.

6. An analytical device according to claim 1, wherein said bibulous sample receiving member protrudes from said casing.

7. A method of using an analytical device according to claim 1, wherein said device is hand-held by means of said cover means enclosing said window means, while said bibulous sample receiving member is introduced into a source of sample liquid, such as a urine stream, and thereafter said cover means is released to expose said window means.

8. A method according to claim 7, wherein after release of said cover means to expose said window means, the same cover means is used to enclose said bibulous sample receiving member.

9. A method according to claim 8, wherein following sample collection and enclosure of said bibulous sample receiving member, said device is hand-held by means of said cover means enclosing said bibulous sample receiving member to facilitate presentation of said window means to means for reading the result of said analysis.

* * * * *

REEXAMINATION CERTIFICATE (4016th)

United States Patent [19]
Senior

[11] B1 5,504,013
[45] Certificate Issued Mar. 14, 2000

[54] ANALYTICAL DEVICES AND METHODS OF USE THEREOF

[75] Inventor: Stephenie J. Senior, Bedford, United Kingdom

[73] Assignee: Unipath Limited, Basingstoke, United Kingdom

Reexamination Request:
No. 90/005,506, Sep. 24, 1999

Reexamination Certificate for:
Patent No.: 5,504,013
Issued: Apr. 2, 1996
Appl. No.: 08/338,150
Filed: Nov. 9, 1994

[30] Foreign Application Priority Data

Nov. 12, 1993 [EP] European Pat. Off. .............. 93309055

[51] Int. Cl.⁷ ...................... G01N 33/558; G01N 33/543; G01N 33/76
[52] U.S. Cl. .............................. 436/165; 422/56; 422/58; 422/61; 436/169
[58] Field of Search ................................. 422/56, 58, 61; 436/165, 169

[56] References Cited

U.S. PATENT DOCUMENTS

| | | | |
|---|---|---|---|
| 3,620,677 | 11/1971 | Morison | 23/253 |
| 3,642,450 | 2/1972 | Eriksson | 23/253 |
| 3,768,979 | 10/1973 | Mead et al. | 23/259 |
| 3,980,436 | 9/1976 | Greenfield et al. | 23/253 R |
| 4,258,135 | 3/1981 | Meunier | 435/301 |
| 4,624,929 | 11/1986 | Ullman | 436/179 |
| 4,635,488 | 1/1987 | Kremer | 73/864.72 |
| 4,678,757 | 7/1987 | Rapkin et al. | 436/169 |
| 4,960,691 | 10/1990 | Gordon et al. | 435/6 |
| 5,275,785 | 1/1994 | May et al. | 422/56 |

FOREIGN PATENT DOCUMENTS

| | | |
|---|---|---|
| 0383619 | 8/1990 | European Pat. Off. . |
| 5/077763 | 10/1993 | Japan . |
| 2204398 | 11/1988 | United Kingdom . |
| WO 93/03673 | 3/1993 | WIPO . |

OTHER PUBLICATIONS

Database WPI, Week 8828, Derwent Publication Ltd., London, GB; AN 88–195635, Jun. 7, 1988.

Database WPI, Week 8748, Derwent Publications Ltd., London, GB; AN 87–339223, Oct. 26, 1987.

*Primary Examiner*—Arlen Soderquist

[57] ABSTRACT

An analytical device for determining the presence and/or concentration of an analyte in a sample liquid comprises a hollow casing; an assay strip within said casing for selectively capturing an analyte in sample liquid applied to the device; a bibulous sample liquid receiving member at or adjacent to a first extremity of said casing which collects sample liquid and transports it into the casing; a window in the casing at a location remote from the first extremity of the casing; and a single cap which can be applied in turn over the window during sample collection, and then over the sample receiving member.

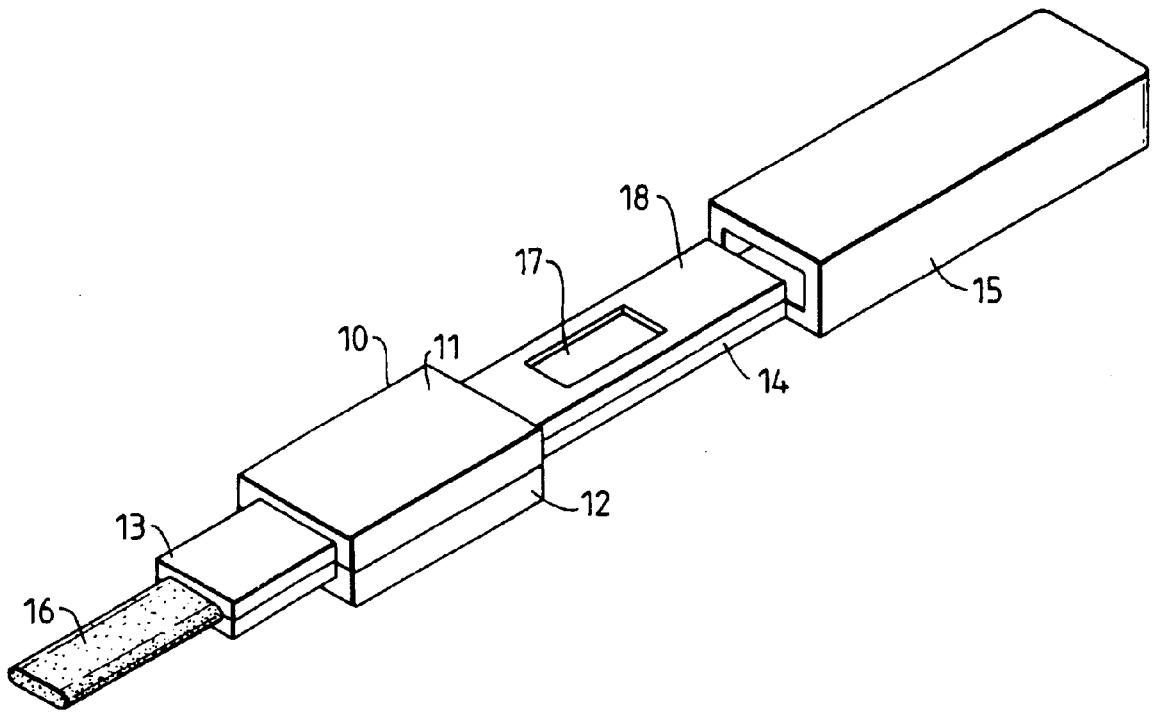

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *